(12) United States Patent
Oida et al.

(10) Patent No.: US 7,227,642 B2
(45) Date of Patent: Jun. 5, 2007

(54) ABSORBANCE MONITOR

(75) Inventors: Takuji Oida, Kyoto (JP); Shigeyuki Akiyama, Kyoto (JP); Masahiko Endo, Kyoto (JP); Norikazu Iwata, Kyoto (JP); Satoshi Inoue, Kyoto (JP); Masahiko Fujiwara, Kyoto (JP)

(73) Assignee: Horiba, Ltd., Kyoto (JP)

( * ) Notice: Subject to any disclaimer, the term of this patent is extended or adjusted under 35 U.S.C. 154(b) by 352 days.

(21) Appl. No.: 10/958,011

(22) Filed: Oct. 4, 2004

(65) Prior Publication Data

US 2005/0082483 A1  Apr. 21, 2005

(30) Foreign Application Priority Data

Oct. 10, 2003  (JP) ............................. 2003-352463

(51) Int. Cl.
*G01N 21/61* (2006.01)
(52) U.S. Cl. ..................... 356/439; 356/440; 250/343
(58) Field of Classification Search ................ 356/433, 356/435, 437, 438, 439, 440, 413; 250/343, 250/345
See application file for complete search history.

(56) References Cited

U.S. PATENT DOCUMENTS 5,092,342 A * 3/1992 Hattendorff et al. ........ 250/343
5,282,473 A * 2/1994 Braig et al. .................. 250/343
5,693,945 A * 12/1997 Akiyama et al. ........... 250/345
5,773,828 A * 6/1998 Akiyama et al. ........... 250/343

FOREIGN PATENT DOCUMENTS

| JP | 2903457 | 3/1993 |
|---|---|---|
| JP | 8-43302 | 2/1996 |

* cited by examiner

*Primary Examiner*—Richard A. Rosenberger (57) ABSTRACT

This invention relates to a multi-component absorbance monitor, and the object is to provide a general-purpose and highly accurate compact absorbance monitor. Disclosed is an absorbance monitor including a light source, a sample cell and a plurality of detectors as elements, wherein a light collecting member is arranged between the light source and one detector, and an inside wall of the light collecting member has a site for guiding a part of light from the light source, that is, a light guiding opening, and light from the light guiding opening enters another detector. Preferably, the light collecting member lies between the light source and the sample cell. Preferably, an optical element used for another detector described above is arranged in the light guiding opening and adjacently to a light path formed by the light collecting member.

15 Claims, 7 Drawing Sheets

ABSORBANCE MONITOR

BACKGROUND OF THE INVENTION

1. Field of the Invention

The present invention relates to an absorbance monitor for measuring the concentrations of specific components in various fluids and is particularly useful in a highly accurate and compact fluid concentration measuring instrument for measuring a plurality of components present in a sample.

2. Description of the Related Art

In various production processes in recent years, it is essential to control the concentrations of substances controlled and various interfering substances, and highly accurate measuring instruments capable of coping with various uses are required. Conventionally, general-purpose absorbance monitors capable of measuring many kinds of components simultaneously in the same constitution, such as a non-dispersive infrared analyzer (referred to hereinafter as "NDIR") and a non-dispersive ultraviolet analyzer (referred to hereinafter as "NDUV"), are often used. Such absorbance monitors do basically not contact a sample and are thus useful as in-line monitors in various processes.

Figure 8:
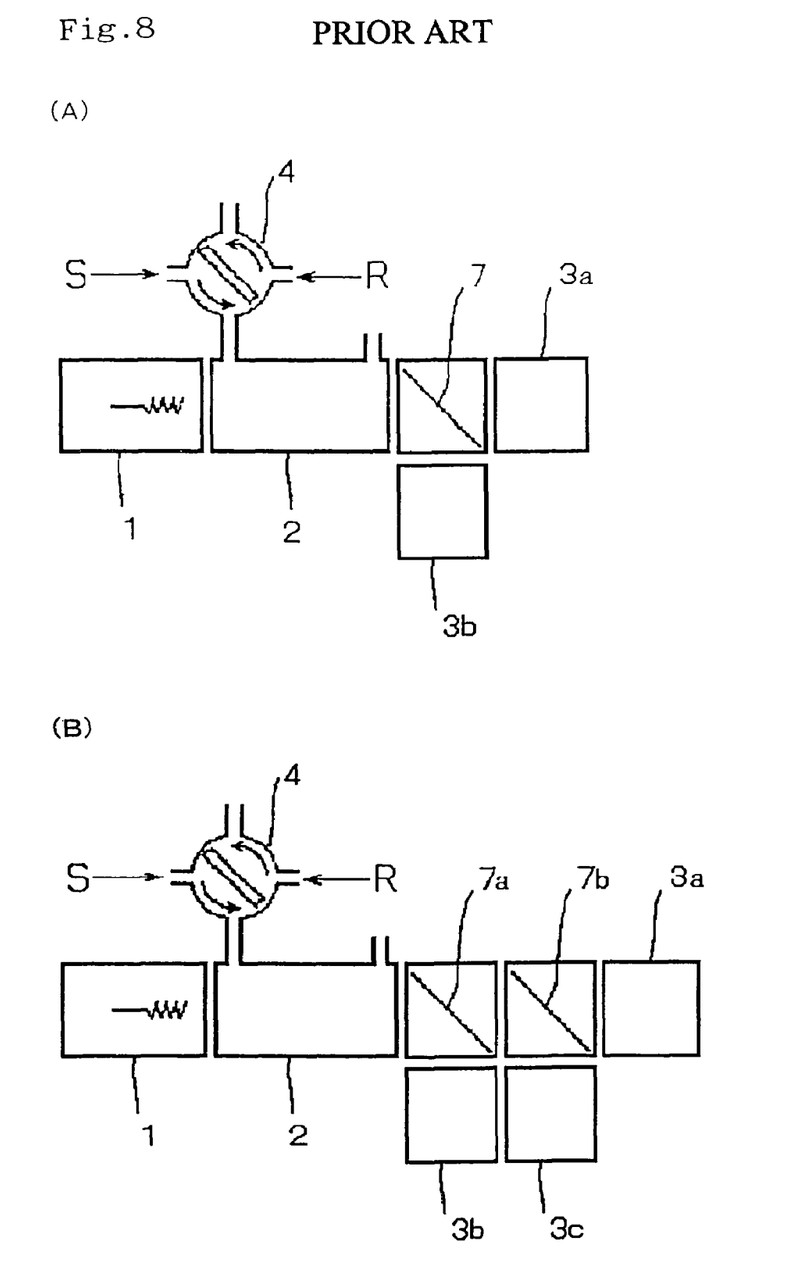
FIG. 8 is a schematic view showing one constitutional example of an absorbance monitor in the related art.

Specifically, there is practically used a method of using a stable and multi-component measuring absorbance monitor illustrated in FIGS. 8(A) and (B) wherein optical elements 7a and 7b between a light source 1 and a detector 3 are arranged with a predetermined inclination relative to a light path, to diverge and introduce light into a plurality of detectors 3a, 3b and 3c such that a change in absorbance in a sample cell 2 can be detected (see, for example, Japanese Patent No. 2903457).

That is, when a power source (not shown) for the light source supplies electric power, an infrared ray from the light source 1 enters via the sample cell 2 into the detectors 3a, 3b and 3c. Optical filters 7a and 7b permitting an infrared ray in a wavelength range corresponding to a measurement component to penetrate selectively therethrough are arranged between the light source 1 and detectors 3a, 3b and 3c, and a change in the amount of only the infrared ray absorbed by a measurement component in a fluid sample introduced into the sample cell 2 is detected. A fluid switch 4 is used in modulation by periodically switching a fluid sample S and a standard (reference) fluid R with each other, and a change in the amount of the absorbed infrared ray in the sample cell is taken out as an alternating current signal, and this detector output is amplified with a preamplifier (not shown), then inputted into a signal processing unit (not shown), subjected to signal processing such as commutation and calculated to indicate the concentration of the component in an indicator (not shown).

In place of the fluid modulation system described above, there are known a mechanical light intermittence system wherein a chopper driven by a motor is arranged in the middle of the optical system to convert the infrared ray into an intermittent light to be introduced into a detector and a light modulation system NDIR wherein in place of the chopper, a light source voltage modulation means is arranged between a power source and a light source, to modulate electric power applied to the light source by turning on and off electric power. Using such constitution, not only measurement methods of using the NDIR but also measurement methods of using NDUV are proposed and practically used (see, for example, JP08-43302A).

In a sample containing a plurality of components, however, the respective components are often significantly different in concentration from one another, and the absorbance monitors described above in the related art may cause the following problems.

One problem lies in measurement errors caused generally by a relationship similar to light absorption characteristics called the Lambert-Beer law expressed in the following equation (1), between the quantity of light absorbed (that is, the concentration of component to be measured) and detector output.

$$I_0/I = A \times \log(\epsilon c d) \qquad (1)$$

where $I_0$ and $I$ represent the quantity of incident light and the quantity of penetrated light respectively in a sample cell, and $\epsilon$, $c$ and $d$ represent light absorption coefficient, concentration of objective substance, and cell light path length, respectively.

That is, in the optical system using one sample cell, the quantity of light absorbed is significantly varied depending on the intended component so that when a low-concentration sample is measured, an output region of good linearity can be utilized, while when a high-concentration component is measured, the linearity of output is deteriorated, thus causing a difference in reading miscalculation and a difference in temperature characteristics. Accordingly, two or more optical systems different in cell length are often used in one analyzer, resulting in an enlargement of the analyzer.

When the number of components to be measured in the constitution shown in FIG. 8(A) is increased, the constitution in FIG. 8(B) is used and an additional optical element 7b should be used in this constitution. So due to optical loss caused by a larger size of the optical system and an addition of the part, there may arise a problem of deterioration in detection sensitivity.

Figure 9:
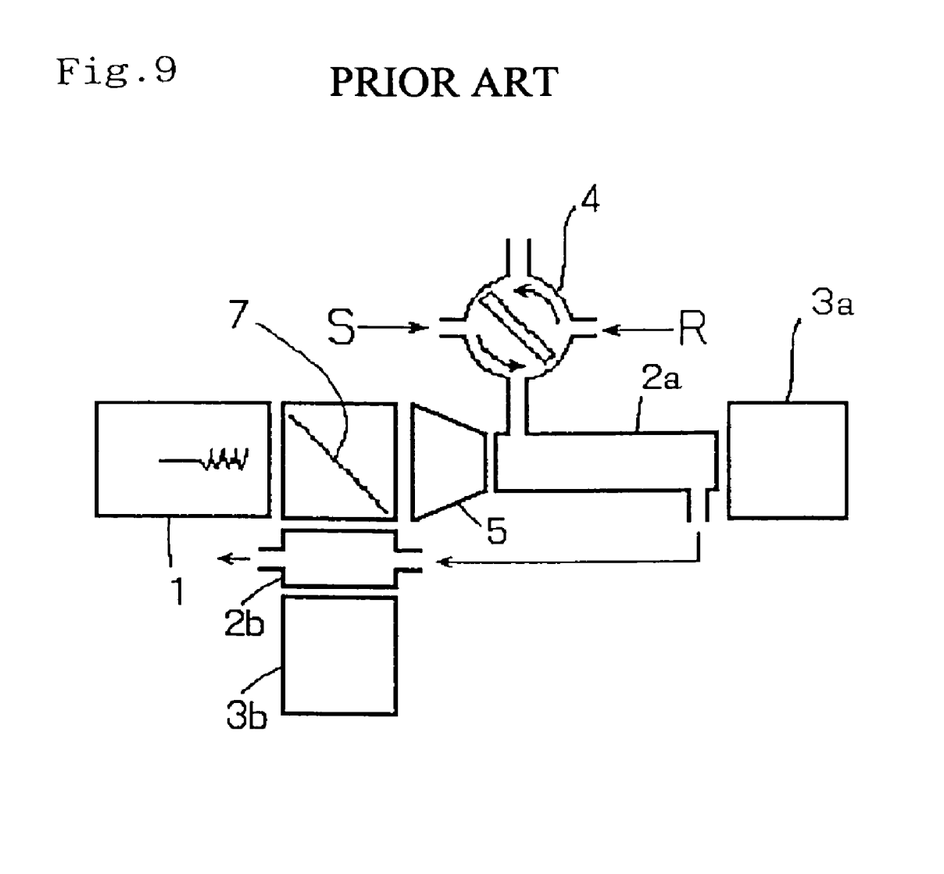
FIG. 9 is a schematic view showing another detailed constitutional example of an absorbance monitor in the related art.

For the purpose of reducing a sample flow in the optical system described above, the aperture diameter of the sample cell may be decreased, but the same problem may also arise in this case. Specifically, there is an optical system wherein a light collecting member 5 or a sample cell 2b is additionally used as shown in FIG. 9, but there may arise a problem of deterioration in detection sensitivity due to optical loss caused by addition of the part.

SUMMARY OF THE INVENTION

To solve the problem described above, the object of the present invention is to provide a general-purpose absorbance monitor for measuring a plurality of components highly accurately.

To solve the problem, the present inventors made an extensive study, and as a result, they found that the object can be achieved by the following absorbance monitor, thus arriving at the present invention.

The present invention provides an absorbance monitor including a light source, a sample cell and a plurality of detectors as elements, wherein a light collecting member is arranged between the light source and the detector, and an inside wall of the light collecting member has a site for guiding a part of light from the light source, that is, a light guiding opening, and light from the light guiding opening enters another detector. The present inventors found that when the aperture diameter of a light path extending from a light source to a detector is changed, a light collecting member is arranged to collect a part of light from an inside wall of the optical member thereby using the optical member in common, and the incident angle of light which can be taken out from the guiding opening is limited thereby enabling acquisition of light of very stable quantity, thus providing a general-purpose absorbance monitor wherein a plurality of components can be measured in a high accuracy. The absorbance monitor is also very excellent in that an optical system in a later stage can be composed very flexibly because no optical element is arranged in the light path of the light collecting member. The analyzer may be composed not only of a single sample cell and a single optical element but also of two or more sample cells and optical elements, as described later.

In the absorbance monitor described above, the light collecting member lies preferably between the light source and the sample cell. The present inventors found that the technical effect described above is more effective under conditions where the quantify of light from the light guiding opening is scarcely attenuated, and the light collecting member is arranged preferably adjacently to a light path having a large quantity of light with many angular components, that is, adjacently to a light source, so that the attenuation of reflected light on a light path-forming surface such a wall of a sample cell does not occur.

Further, an optical element used for another detector described above is arranged preferably in the light guiding opening and adjacently to a light path formed by the light collecting member. By this arrangement, an optical loss by the light guiding opening arranged on a part of the light path in the optical system can be reduced, and the wavelength characteristics of reflected light on the optical element can be effectively utilized.

DETAILED DESCRIPTION OF THE INVENTION

Hereinafter, embodiments of the invention are described in detail.

Figure 1:
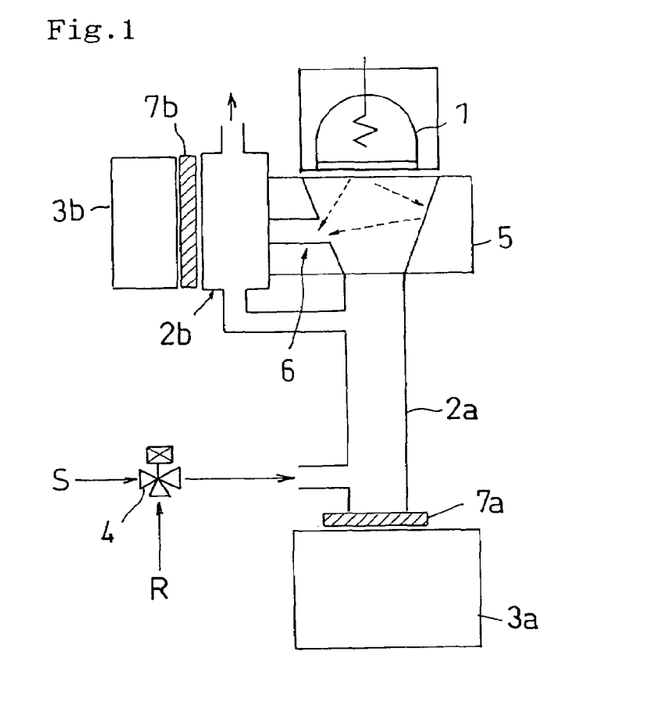
FIG. 1 is a schematic view showing a first constitutional example of the absorbance monitor of the present invention.

FIG. 1 shows a first constitutional example of the absorbance monitor of the present invention. In FIG. 1, an optical system is formed from a light path comprising a light source 1 receiving electric power from an electric source (not shown), a light collecting member 5, a sample cell 2a, an optical element 7a and a detector 3a, and a light path having a light guiding path 6 via a part of an inside wall of the light collecting member 5, a sample cell 2b, an optical element 7b and a detector 3b. A fluid is introduced from the sample cell 2a into the sample cell 2b, where a sample fluid S and a reference fluid R are switched periodically with each other using a fluid switch 4, whereby a change in the amount of absorbed infrared ray in each of the sample cells 2a and 2b can be taken out as an alternating current signal by each of the detectors 3a and 3b (fluid modulation). As described above, each detector output is amplified with a preamplifier (not shown), then inputted into a signal processing unit (not shown), subjected to signal processing such as commutation and calculated to indicate the concentration in an indicator (not shown).

The present invention is characterized in that when the aperture diameter of a light path extending from the light source 1 to the detectors 3a and 3b is changed, the optical element for diverging light is used in common by taking a part of light from an inside wall of the light collecting member 5, and simultaneously the incident angle of light which can be taken out from the guiding opening is limited. That is, the necessary function can be secured not by providing two members as shown in FIG. 9 described above, but by one light collecting member 5. Further, it is characterized in that because the light collecting member can diverge the light path without an optical element in the light path, a very flexible constitution of the optical system in a later stage can be achieved. For forming the optical element having an angle of inclination, an optical element of large opening diameter is required, but the present invention is superior in that the optical system for both the components can be composed of an optical element of small diameter.

Figure 2:
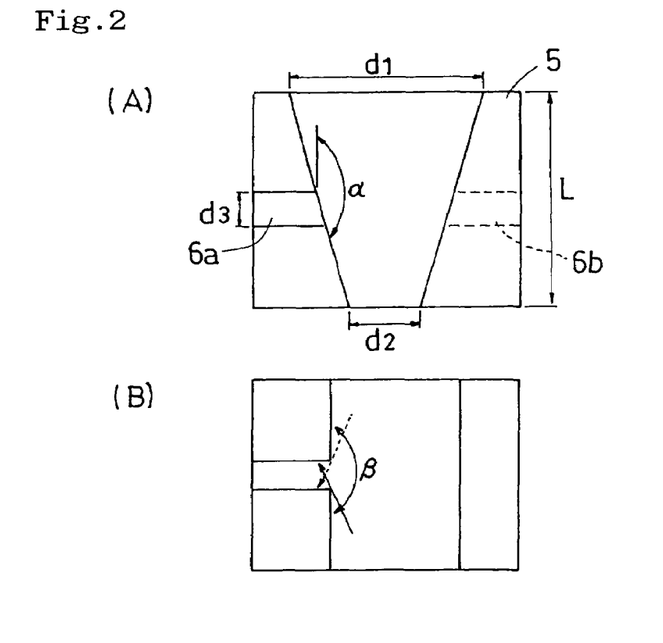
FIG. 2 is a schematic view showing a detailed constitutional example of the light collecting member in the present invention.

As illustrated in FIG. 2(A), light entering the light guiding path 6 enters in a direction in the range of angle α, but light (reversing light) particularly in the direction from the sample cell 2a scarcely enters the path 6. So light entering the light guiding path 6 does not undergo influence including a change in the quantity of light from the direction of the sample cell 2a, and very stable quantity of light can be taken out. In the generally conceivable case where the light path is perpendicular to the light guiding path 6 as shown in FIG. 2(B), light entering the light guiding path 6 enters in the direction of angle β, that is, a direction of about 180°, and may undergo influence including a change in the quantity of reversing light. The present invention has an effect of eliminating such influence, and highly contributes to the stability of measurement by the detector 3b.

As shown in FIG. 2(A), the light guiding path can compose a plurality of light paths including 6a (solid line) and 6b (broken line). The light path refers to every path of light entering from the light source to each detector.

The light collecting member 5 does not always require the inside wall to be straight in insofar as the inside wall has an angle of less than 180° to the light path and has a different aperture diameter so as to have the function described above, and the light collecting member is required to has no special shape, but preferably forms a tapered light path as illustrated in FIG. 2(A). Its material and manufacturing method are not particularly limited, but usually a metallic or resin light collecting member is often used for processability, and its inside wall surface is subjected to polishing treatment or plating treatment or provided with a sleeve material thereby increasing reflectance of light.

The diameter $d_1$ of the wide aperture, the diameter $d_2$ of the narrow aperture, the diameter $d_3$ of the light guiding path 6, and the length L of the light path are not particularly limited, and are established depending on light density of the light source 1 and the internal diameter of the sample cell 2.

Specifically, examples of actual measurement in FIG. 2(A) are shown in Table 1. The output of the detector 3b (output for 4.92% $CO_2$) is shown upon change in the length L of the light path in the light collecting member 5 having $d_1$ of $\phi$16 mm, $d_2$ of $\phi$7.5 mm and $d_3$ of $\phi$2 mm.

TABLE 1

| Item | Sample 1 | Sample 2 | Sample 3 |
|---|---|---|---|
| Light path (mm) | 15 | 20 | 25 |
| Output of the detector (mV) | 197 | 199 | 199 |

As shown in Table 1, there was substantially no change in the output of the detector 3b. It can be estimated that very stable output can be obtained when the angle α is higher than a predetermined value.

In the foregoing, the detector 3a can directly receive light from the light source 1 and is thus preferably used in measurement of components requiring most highly sensitive detection. For example, the NDIR used in a combustion exhaust gas measuring instrument is provided with a nitrogen monoxide (NO) detector as detector 3a and a carbon dioxide ($CO_2$) detector as detector 3b, whereby NO of low IR absorbance can be measured highly sensitively at a low concentration of several tens to hundreds ppm, and simultaneously $CO_2$ of high IR absorbance can be measured highly sensitively at a high concentration of several to ten or more %, and the two can be measured simultaneously under the optimum conditions.

As a matter of course, the modulation method and the constitution of the optical system such as arrangement of elements such as the sample cell 2 between light source 1 and detector 3, the optical element 7 and the light collecting member 5 are not limited to those of FIG. 1.

The sample cells 2a and 2b often have a structure wherein optical crystals are fixed to both sides of a cylindrical tube made of resin or metal such as stainless steel or aluminum having a sample inlet and outlet.

The detectors 3a and 3b in NDIR include a pneumatic detector with a built-in condenser microphone or flow sensor, or a solid detector using a pyro-optical device or a thermopile device, and the former is a detector excellent in detection sensitivity and selectivity, while the latter is a detector excellent in mass production, miniaturization and general-purpose properties, and suitable one is selected depending on use. In NDUV, a photomultiplier, and a solid detector such as a photocell or a photodiode, can be mentioned, and the former is a detector excellent in detection sensitivity and selectivity, while the latter is a detector excellent in mass production, miniaturization and general-purpose properties.

The optical elements 7a and 7b refer to a broad concept including an optical filter having a multilayer film formed on a substrate and a general base material through which light in a specific wavelength range penetrates. The former includes, for example, a band pass filter (BPF) through which light in a specific wavelength range penetrates, a long pass filter (LPF) through which light in a longer-wavelength range than a specific wavelength penetrates, and a short pass filter (SPF) through which light in a shorter-wavelength range than a specific wavelength penetrates. The latter includes base materials through which ultraviolet to infrared rays penetrate, such as quartz ($SiO_2$) through which light of wavelength up to about 3.5 μm penetrates, sapphire ($Al_2O_3$) through which light up to about 4 μm penetrates, lithium fluoride (LiF) through which light up to about 6 μm penetrates, calcium fluoride ($CaF_2$) through which light up to about 8 μm penetrates, barium fluoride ($BaF_2$) through which light up to about 12 μm penetrates, and sodium chloride (NaCl) through which light up to about 13 μm penetrates. A beam splitter utilizing the surface reflection of the base material itself or having a reflective film formed on the surface of the base material is used.

Figure 3:
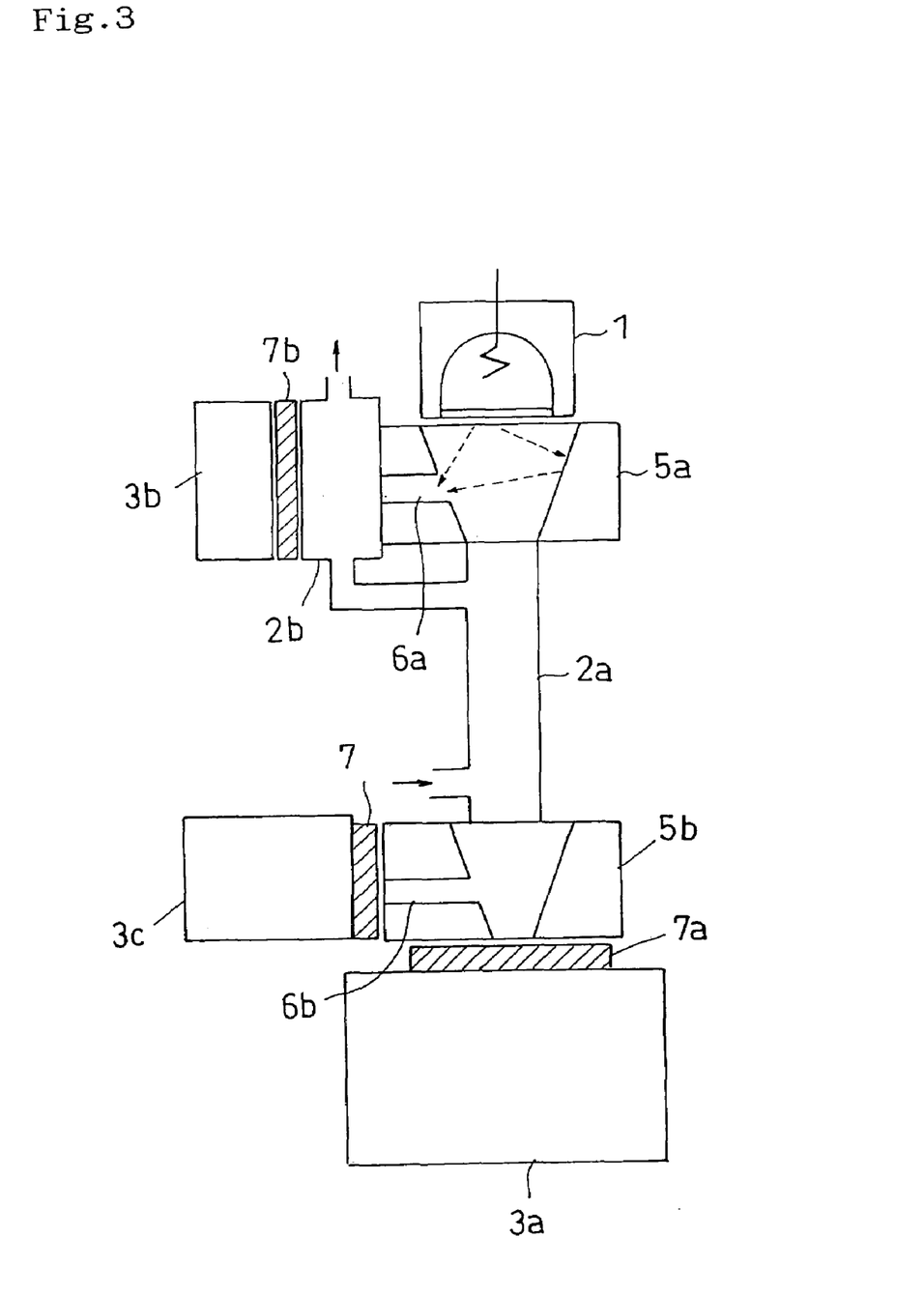
FIG. 3 is a schematic view showing a second constitutional example of the absorbance monitor of the present invention.

FIG. 3 shows a second constitutional example of the present invention, which has light collecting members 5a and 5b. This example is characterized in that a light collecting member 5b is arranged between the sample cell 2a and the detector 3a in the first constitutional example in order to measure an additional component. That is, as described above, the light collecting member 5a can diverge the light path without an optical element in the light path, so that when three or more components are to be measured, an additional light collecting member 5b is arranged in a later stage, whereby the detector 3a arranged at the smaller aperture side of the light collecting member 5a is irradiated with the majority of incident light from the larger aperture side, while the detector 3c is irradiated with a part of the light. Usually, limitation of wavelengths by an optical element arranged in the light path can often lead to successful improvement of selectivity, but results in limitation of use of the transmitted or reflected light, thus failing to cope with general-purpose properties sometimes. In this case, general-purpose properties can be effectively secured by diverging the light path without arranging an optical element. As a matter of course, it is possible to achieve the technical effect of the invention, that is, to enable use of an optical element of small aperture for both the detectors and to improve measurement stability of the detector 3c.

For example, the NDIR used in a combustion exhaust gas measuring instrument is provided with a NO detector as detector 3a, a $CO_2$ detector as detector 3b and a sulfur dioxide ($SO_2$) detector as detector 3c, whereby NO of low IR absorbance can be measured highly sensitively at a low concentration of several tens to hundreds ppm, and simultaneously $CO_2$ of high IR absorbance can be measured highly sensitively at a high concentration of several to ten or more %, and $SO_2$ of high IR absorbance can be measured highly sensitively at a low concentration of several tens to hundreds ppm, and these three components can be measured simultaneously under the optimum conditions.

An absorbance monitor wherein two light collecting members 5a and 5b are arranged is illustrated above, and in respect of the functions of the light collecting members, it is more preferable that the light collecting member 5a lies between the light source 1 and sample cell 2a as shown in FIG. 3. As shown in the arrow (broken line) in FIG. 3, the majority of light entering the light guiding path 6a is a reflected light occurring between the light guiding path 6a and light source 1, and the quantity of the reflected light is higher and more effective near to a light path having a large quantity of light with many angular components, that is, near to the light source. As the reflected light passes thorough various optical members such as the sample cell, the light is attenuated by the wall forming the light path, thus making it more preferable to adopt conditions for reducing such attenuation of the quantity of light. Such technical effect can further reduce the light path diameter of the light guiding path 6a, thus advantageously reducing the optical loss caused by arranging the light guiding path 6a.

Figure 4:
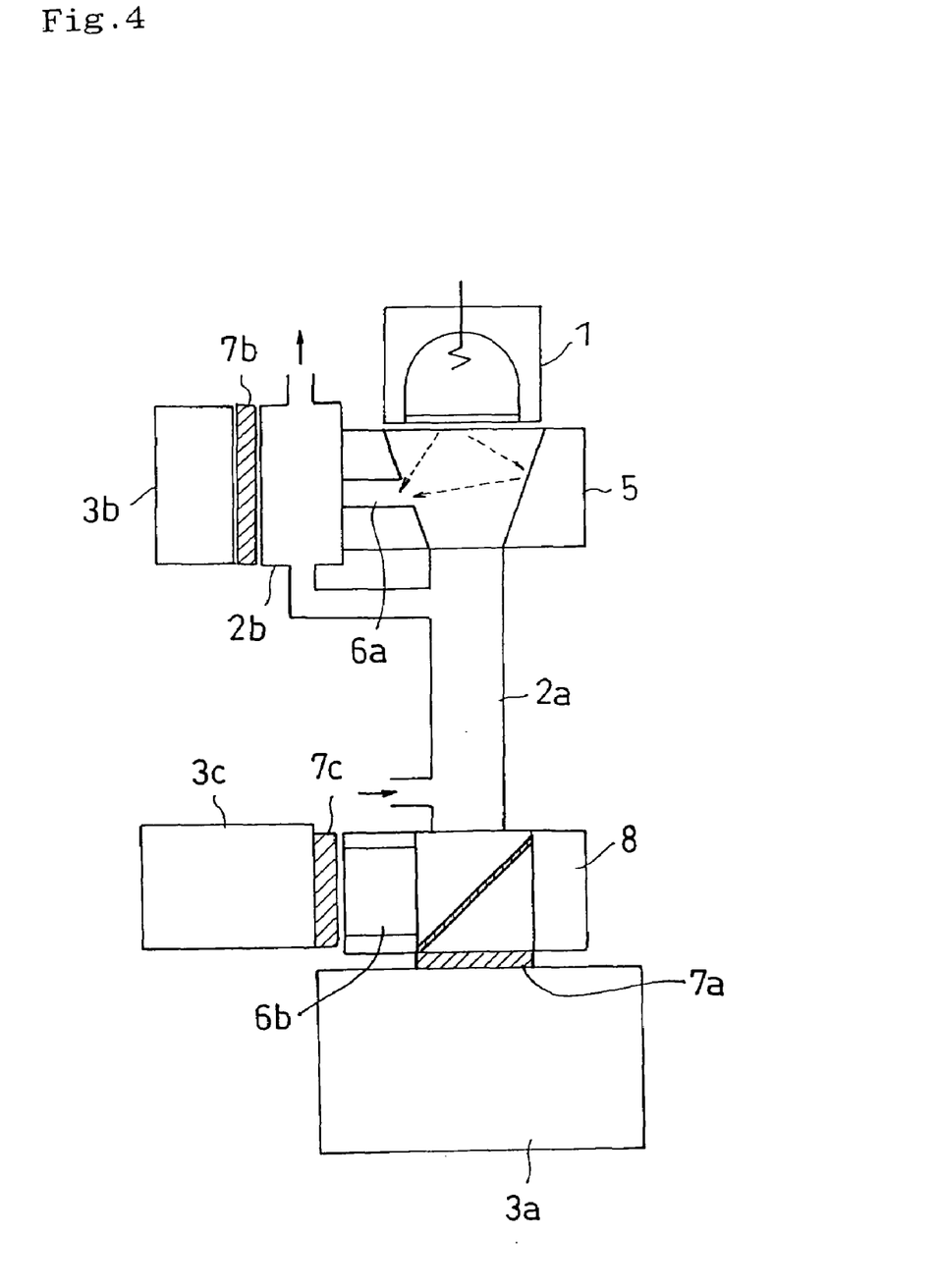
FIG. 4 is a schematic view showing a third constitutional example of the absorbance monitor of the present invention.

FIG. 4 shows a third constitutional example of the invention, wherein a combination of a light collecting member and an optical element part is arranged in the same optical system. In this example, an optical element part 8 is used in place of the light collecting member in the second constitutional example, thus securing the advantage of diverging the light path without an optical element in the light path by the light collecting member 5, and simultaneously attaining advantages in detection sensitivity and selectivity by suitable combination with the optical element part 8. That is, even if light passes through the light collecting member 5, the quantity of light is scarcely attenuated, and the whole of reflected light can be utilized by the optical element part 8, and simultaneously the wavelength characteristics of reflected light on a specific optical element (particularly an optical filter) can be effectively utilized.

For example, the NDIR used in a combustion exhaust gas measuring instrument is provided with an NO detector as detector 3a, a $CO_2$ detector as detector 3b and a carbon monoxide (CO) detector as detector 3c, whereby NO of low IR absorbance can be measured highly sensitively at a low concentration of several tens to hundreds ppm, and simultaneously $CO_2$ of high IR absorbance can be measured highly sensitively at a high concentration of several to ten or more %, and CO of low IR absorbance can be measured highly sensitively at a relatively high concentration of several hundreds to thousands ppm, and these three components can be measured simultaneously under the optimum conditions. That is, the measurement accuracy of NO and $CO_2$ can be secured by the light collecting member 5, while the measurement accuracy of CO can be secured by utilizing the optical element part 8, that is, BPF characteristics of NO.

Figure 5:
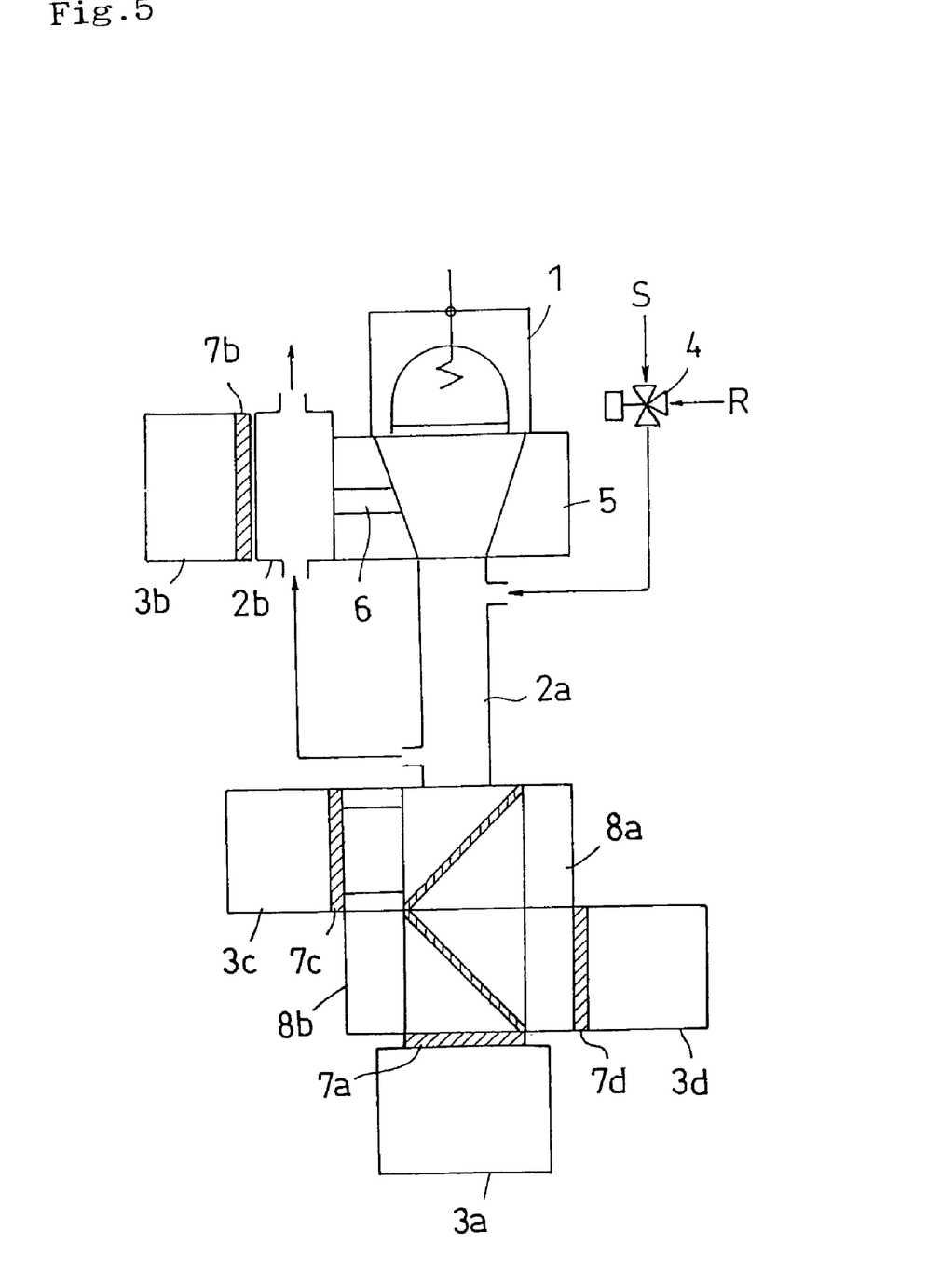
FIG. 5 is a schematic view showing a fourth constitutional example of the absorbance monitor of the present invention.

FIG. 5 shows a fourth constitutional example of the invention, wherein a combination of one light collecting member 5 and two optical element parts 8a and 8b is arranged in the same optical system. This example is one optical system as a combination of the constitutional examples described above, to achieve advantages in detection sensitivity and selectivity by suitably combining the advantage of the light collecting member 5 with the advantage of the optical element parts 8a and 8b.

For example, the NDIR used in a combustion exhaust gas measuring instrument is provided with an NO detector as detector 3a, a $CO_2$ detector as detector 3b, a carbon monoxide (CO) detector as detector 3c and a $SO_2$ detector as detector 3d, whereby NO of low IR absorbance can be measured highly sensitively at a low concentration of several tens to hundreds ppm, and simultaneously $CO_2$ of high IR absorbance can be measured highly sensitively at a high concentration of several to ten or more %, CO of low IR absorbance can be measured highly sensitively at a relatively high concentration of several hundreds to thousands ppm and $SO_2$ of high IR absorbance can be measured highly sensitively at a low concentration of several tens to hundreds ppm, and these four components can be measured simultaneously under the optimum conditions. That is, the measurement accuracy of NO and $CO_2$ can be secured by the light collecting member 5, while the measurement accuracy of CO and $SO_2$ can be secured by utilizing the optical element parts 8a and 8b.

Figure 6:
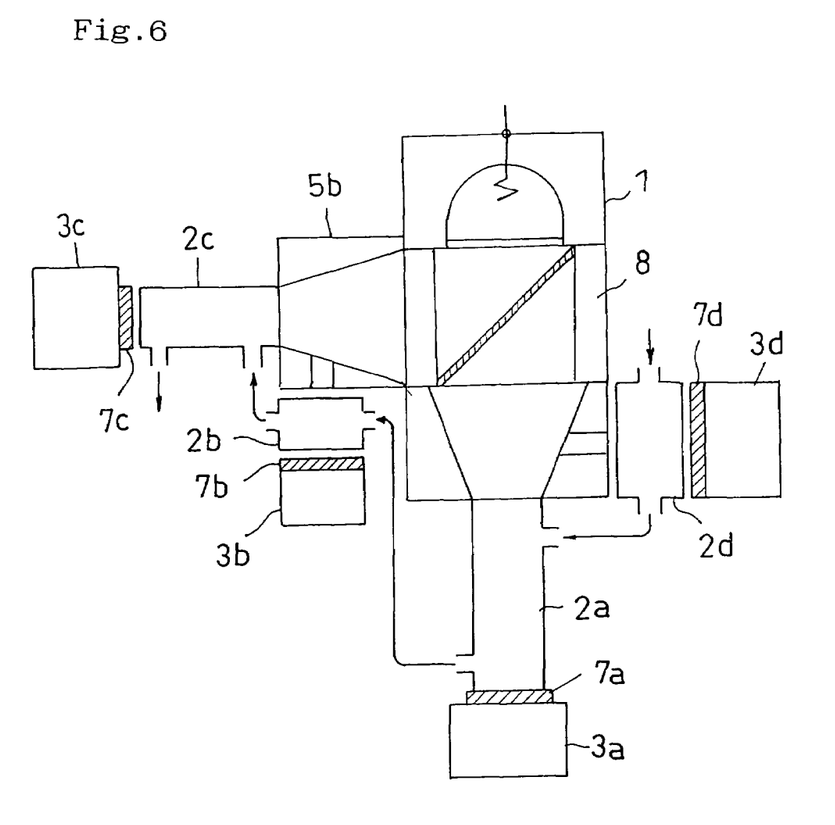
FIG. 6 is a schematic view showing a fifth constitutional example of the absorbance monitor of the present invention.

FIG. 6 shows a fifth constitutional example of the invention, wherein a combination of two light collecting members 5a and 5b and one optical element part 8 is arranged in the same optical system. This example is one optical system as a combination of the constitutional examples described above, to achieve advantages in detection sensitivity and selectivity by suitably combining the advantage of the light collecting members 5a and 5b with the advantage of the optical element part 8. This example is particularly advantageous where there are a plurality of sample cells (2a and 2c) requiring a change in aperture diameter as shown in FIG. 6.

For example, the NDIR used in a combustion exhaust gas measuring instrument is provided with an NO detector as detector 3a, a $CO_2$ detector as detector 3b, a carbon monoxide (CO) detector as detector 3c and a $SO_2$ detector as detector 3d, whereby NO of low IR absorbance can be measured highly sensitively at a low concentration of several tens to hundreds ppm, and simultaneously $CO_2$ of high IR absorbance can be measured highly sensitively at a high concentration of several to ten or more %, CO of low IR absorbance can be measured highly sensitively at a relatively high concentration of several hundreds to thousands ppm and $SO_2$ of high IR absorbance can be measured highly sensitively at a low concentration of several tens to hundreds ppm, and these four components can be measured simultaneously under the optimum conditions. That is, when 5 μm LPF is used as an optical element in the optical element part 8, reflected light having a wavelength range of 5 μm or less is utilized for measurement of CO (usually light with a central wavelength of 4.7 μm is utilized) and $CO_2$ (usually light with a central wavelength of 4.3 μm is utilized), while transmitted light having a wavelength range of 5 μm or more is utilized for measurement of NO (usually light with a central wavelength of 5.3 μm is utilized) and $SO_2$ (usually light with a central wavelength of 7.3 μm is utilized), thus enabling improvement in selectivity and securing measurement accuracy by establishing the sample cell diameter and cell length suitable for the respective components.

Figure 7:
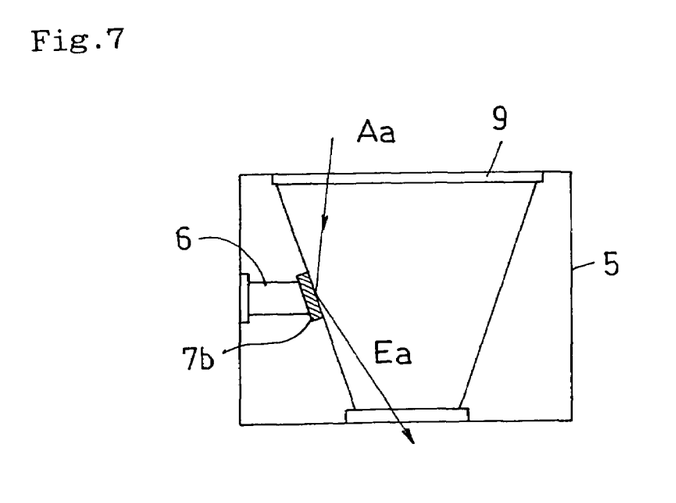
FIG. 7 is a schematic view showing another detailed constitutional example of the light collecting member in the present invention.

In the constitutional examples described above, it is preferable that the optical element used in detection of light entering the light guiding path is arranged in the light guiding opening in the light collecting member and adjacently to the light path formed by the light collecting member. As shown in FIG. 7, an optical element 7b is arranged on an inside wall of the light collecting member 5 thereby reducing an optical loss and effectively utilizing the wavelength characteristics of reflected light on the optical element.

That is, in the former, light such as light Aa shown in FIG. 7, which is the cause of conventional optical loss i.e. deterioration in the detection sensitivity of detector 3a, is reflected by the optical element 7b arranged adjacently to the light path and is thus applied to the detector 3a, to achieve an effect of increasing the quantity of light on the detector 3a. This effect is varied depending on various conditions such as the aperture diameter of the light guiding path 6 and the light path diameter of the light collecting member 5, and is particularly influenced when the light collecting member 5 is arranged adjacently to the light source 1, to successfully bring about an effect of attaining sensitivity higher by several percents in actual measurements than the case where an introducing path having the same diameter as that of the light path is provided.

In the latter, when an optical filter for measurement of $CO_2$ as described above is used as the optical element 7b arranged in the light guiding opening, light excluding light of a central wavelength of 4.3 μm is introduced as reflected light into the sample cell 2a, thus achieving the above effect and simultaneously contributing to improvement in the selectivity of detector 3a etc. Such effects are varied depending on various conditions such as the aperture diameter of the light guiding path 6 and the light path diameter of the light collecting member 5, but when the light collecting member 5 is arranged adjacently to the light source 1, significant effects can be achieved.

FIG. 7 shows a structure wherein an optical window 9 is arranged in the light path of the light collecting member 5, but the constitution of the present invention is not limited to that of FIG. 7, and the optical window 9 is arranged depending on each member in the optical system.

The techniques of the present invention described above are applicable to absorbance monitors such as NDIR and NDUV, to provide general-purpose absorbance monitors for measuring samples containing a plurality of components at high accuracy in a broad range.

As described above, light of very stable light quantity can be taken out by arranging a light collecting member taking a part of light from an inside wall of an optical element. Accordingly, there can be provided a general-purpose multi-component absorbance monitor for measuring a plurality of components at high accuracy.

Particularly, the light collecting member is arranged between a light source and a sample cell, to achieve measurement under conditions where the quantity of light from a light guiding opening is scarcely attenuated, thus utilizing the above-described technical effect more effectively.

Further, another optical element is arranged in the light guiding opening thereby reducing an optical loss and achieving effective utilization of the wavelength characteristics of reflected light on the optical element.

What is claimed is:

1. An absorbance monitor for measuring a plurality of components in a sample, comprises:
   a light source;
   a sample cell;
   a plurality of detector units, each detector unit respectively measuring a different component in the sample; and
   a first light directing member mounted between the light source and the sample cell for directing a first predetermined quantity of the entire wavelength range of light from the light source to a first detection unit of the plurality of detector units and directing a second predetermined quantity of the entire wavelength range of light from the light source to a second detector unit of the plurality of detector units,
   wherein the first light directing member has a light truncated light passageway with a first light transmitting passageway extending at an angle to an axis of the light truncated passageway from the light truncated passageway to the first detector unit.

2. The absorbance monitor of claim 1 wherein the first light transmitting passageway is hollow.

3. The absorbance monitor of claim 1 wherein a light truncated passageway surface is reflective to light from the light source.

4. The absorbance monitor of claim 1 wherein the light truncated passageway surface is conical.

5. The absorbance monitor of claim 1 wherein the second detector unit is aligned on the axis of the light truncated passageway.

6. The absorbance monitor of claim 1 wherein a reflective coating is provided in an interior surface of the light truncated passageway.

7. The absorbance monitor of claim 1 wherein the first light directing member has a hollow tapered light passageway mounted adjacent the light source with the hollow tapered light passageway progressively becoming smaller as it extends from the light source.

8. The absorbance monitor of claim 7 further including an optical filter to limit the specific wavelength range positioned before the first detector unit.

9. The absorbance monitor of claim 7 further including a second light directing member spaced from and receiving light that has passed through the first light directing member.

10. The absorbance monitor of claim 7 wherein a second light directing member is mounted between the light source and the sample cell and a beam splitter unit directs light of different wavelengths to respectively the first light directing member and the second light directing member.

11. A combustion exhaust gas measuring instrument comprising:
    a light source for providing a wide range of wavelengths;
    a first light directing member mounted adjacent the light source having a hollow tapered light passageway with a first light transmitting passageway extending at an angle to an axis of the hollow tapered light passageway for transmitting light;
    a sample cell assembly for receiving the combination exhaust gas and transmitting the combustion exhaust gas to contact light transmitted by the respective light passageways; and
    a plurality of detector units including a first detector unit aligned with the hollow tapered light passageway and a second detector unit aligned with the first light transmitting passageway whereby components within the combustion exhaust gas can be measured.

12. The combustion exhaust gas measuring instrument of claim 11 further including a beam splitter unit aligned with the hollow tapered light passageway after the light has passed through the sample cell assembly, the beam splitter unit directs light to respectively the first detector unit and a third detector unit whereby three different components within the combustion exhaust gas can be measured.

13. The combustion exhaust gas measuring instrument of claim 12 wherein the beam splitter unit directs light to a fourth detector unit whereby $CO_2$, CO, $SO_2$, and NO are measured by the first to fourth detector units.

14. The combustion exhaust gas measuring instrument of claim 11 further including a second light directing member having a hollow tapered light passageway with a second light transmitting passageway extending at an angle to an axis of the hollow tapered light passageway for transmitting light and mounted between the light source and the sample cell assembly, a third detector unit aligned with the second light transmitting passageway and a fourth detector unit aligned with the axis of the second light directing member, wherein the first to fourth detector units, each measures one of $CO_2$, CO, $SO_2$, and NO in the combination exhaust gas.

15. An absorbance monitor for measuring a plurality of components in a sample, comprises:
    a light source;
    a sample cell;
    a plurality of detector units, each detector unit respectively measuring a different component in the sample; and
    a first light directing member mounted between the light source and the sample cell for directing a first predetermined quantity of the entire wavelength range of light from the light source to a first detection unit of the plurality of detector units and directing a second predetermined quantity of the entire wavelength range of light from the light source to a second detector unit of the plurality of detector units,
    wherein the first light directing member has a first hollow tapered light passageway mounted adjacent the light source with the first hollow tapered light passageway progressively becoming smaller as it extends from the light source;

a second light directing member, spaced from and receiving light that has passed through the first light directing member has a second hollow tapered passageway; and a second light transmitting passageway extending at approximately a right angle to an axis of the hollow tapered light passageway;

a third detector unit is operatively positioned to receive light from the second light transmitting passageway and the second detector unit is operatively aligned with the axis of the second hollow tapered light passageway.

* * * * *